US012788388B2

(12) United States Patent
York et al.

(10) Patent No.: US 12,788,388 B2
(45) Date of Patent: Nov. 10, 2026

(54) SURGICAL SYSTEMS AND INSTRUMENTS WITH ENHANCED CLEANABILITY

(71) Applicant: Covidien LP, Mansfield, MA (US)

(72) Inventors: Peter A. York, Hamden, CT (US); David M. Chowaniec, Rocky Hill, CT (US); Matthew S. Hartzsch, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 259 days.

(21) Appl. No.: 18/530,620

(22) Filed: Dec. 6, 2023

(65) Prior Publication Data

US 2024/0225630 A1 Jul. 11, 2024

Related U.S. Application Data

(60) Provisional application No. 63/438,332, filed on Jan. 11, 2023.

(51) Int. Cl.
*A61B 17/02* (2006.01)
*A61B 34/30* (2016.01)
*A61M 13/00* (2006.01)

(52) U.S. Cl.
CPC .......... *A61B 17/0281* (2013.01); *A61B 34/30* (2016.02); *A61M 13/003* (2013.01); *A61B 2034/305* (2016.02)

(58) Field of Classification Search
CPC . A61B 90/70; A61B 17/0281; A61B 18/1445; A61B 2017/00398; A61B 2017/00473; A61B 2017/00477; A61B 2034/305; A61B 2090/0813; A61B 34/30; A61M 13/003
See application file for complete search history.

(56) References Cited

U.S. PATENT DOCUMENTS 8,551,115 B2 10/2013 Steger et al.
9,526,560 B2 12/2016 Manzo et al.
10,010,340 B2 7/2018 Hibner et al.
11,129,685 B2 9/2021 Zemlok et al.
2012/0071713 A1 3/2012 Kaye et al.
2015/0245850 A1* 9/2015 Hibner ........... A61B 17/320092 606/171
2015/0374447 A1* 12/2015 Blumenkranz ........... B08B 9/00 134/166 R
2019/0274781 A1 9/2019 Lambrecht et al.
2020/0022766 A1 1/2020 Millman et al.
2021/0022760 A1 1/2021 Traina

OTHER PUBLICATIONS

Extended European Search Report dated Jun. 11, 2024 for European Patnt Application No. 24151155.9, 12 pages.

* cited by examiner

*Primary Examiner* — Scott Luan
(74) *Attorney, Agent, or Firm* — Carter, DeLuca & Farrell, LLP

(57) ABSTRACT

A surgical instrument includes a housing, a shaft, an end effector, and a cleaning assembly. The housing includes a proximal face. The shaft extends distally from the housing and defines a channel. The end effector is disposed adjacent a distal end of the shaft and is configured to manipulate tissue. The cleaning assembly is disposed at least partially within the housing and defines a fluid path extending between the proximal face of the housing and the channel of the shaft.

20 Claims, 9 Drawing Sheets

SURGICAL SYSTEMS AND INSTRUMENTS WITH ENHANCED CLEANABILITY

CROSS-REFERENCE TO RELATED APPLICATION

This application claims the benefit of and priority to U.S. Provisional Patent Application No. 63/438,332, filed Jan. 11, 2023, the entire contents of which is incorporated by reference herein.

BACKGROUND

In some surgical procedures, a wall of a body cavity is raised by pressurization of the body cavity to provide sufficient working space at the surgical worksite and/or to allow improved access and visibility of the surgical worksite. The process of distending the abdomen wall from the organs enclosed in the abdominal cavity is referred to as insufflation. During a laparoscopic procedure, insufflation may be achieved by introducing an insufflation gas, such as carbon dioxide, nitrogen, nitrous oxide, helium, argon, or the like, through a Veress needle or other conduit inserted through the abdominal wall to enlarge the area surrounding the target surgical site to create a larger, more accessible work area. The surgeon and/or robot is then able to perform the procedure within the body cavity by manipulating the instruments that have been extended through surgical access devices, for instance. To maintain the body cavity in an insufflated state, the insufflation gas cannot be permitted to leak out of the cavity through the surgical instruments. Typically, surgical instruments include at least one seal that prevents the insufflation gas from flowing from the body cavity through the surgical instrument.

Additionally, after the surgical instrument is used during a surgical procedure, portions of the surgical instrument may be thoroughly cleaned and/or sterilized to enable the surgical instrument to be reused.

However, since the seal that prevents the escape of insufflation gas is typically at a proximal end of the instrument and coaxial with its longitudinal axis, cleaning ports are not always able to be optimally positioned within the surgical instrument, and commonly result in an L-shaped fluid path, which may reduce the efficiency of cleaning.

SUMMARY

This disclosure relates to a surgical instrument including a housing, a shaft, an end effector, and a cleaning assembly. The housing includes a proximal face. The shaft extends distally from the housing and defines a channel. The end effector is disposed adjacent a distal end of the shaft and is configured to manipulate tissue. The cleaning assembly is disposed at least partially within the housing and defines a fluid path extending between the proximal face of the housing and the channel of the shaft.

In disclosed embodiments, the fluid path is linear along its entire length.

In disclosed embodiments, the shaft defines a longitudinal axis, and the fluid path is coaxial with the longitudinal axis.

In disclosed embodiments, the cleaning assembly includes a gasket disposed at least partially within a groove defined on the proximal face of the housing.

In disclosed embodiments, the cleaning assembly includes a flush port disposed adjacent a proximal end of the fluid path. It is also disclosed that the cleaning assembly includes a luer fitting configured to selectively engage the flush port.

In disclosed embodiments, the cleaning assembly includes a flush tube extending linearly within a majority of the housing.

In disclosed embodiments, the surgical instrument includes a seal disposed adjacent a proximal portion of the shaft. In is also disclosed that the cleaning assembly includes a flush tube extending at least partially through the seal. It is further disclosed that the cleaning assembly includes a flush port disposed adjacent a proximal end of the fluid path. In embodiments, the cleaning assembly includes a flush tube extending between the flush port and the seal.

In disclosed embodiments, the cleaning assembly includes a plug configured to selectively occlude a proximal opening of the fluid path.

In disclosed embodiments, the housing is configured to couple to an interface. When the interface is coupled to the housing, a proximal opening of the fluid path is occluded by the interface.

In disclosed embodiments, the surgical instrument includes a drive member disposed at least partially within the housing, and a drive rod disposed at least partially within the shaft. Actuation of the drive member is configured to manipulate the drive rod to effect a function of the end effector. It is also disclosed that the cleaning assembly includes a flush tube extending linearly within a majority of the housing, and a proximal end of the drive rod is disposed proximally of a distal end of the flush tube.

The disclosure also relates to a cleaning assembly for use with a surgical instrument. The cleaning assembly includes a flush port configured for positioning adjacent a proximal face of a housing of the surgical instrument, a flush tube extending distally from the flush port, and a luer fitting configured to selectively engage a proximal portion of the flush port. The cleaning assembly defines a fluid path through the housing of the surgical instrument, and an entirety of the fluid path is linear.

In disclosed embodiments, the cleaning assembly includes a gasket configured to engage the proximal portion of the flush port.

In disclosed embodiments, the cleaning assembly includes a plug configured to selectively engage the proximal portion of the flush port.

The disclosure also relates to a surgical instrument including a housing, a shaft, and a cleaning assembly. The housing includes a proximal face. The shaft extends distally from the housing and defines a channel. The cleaning assembly is disposed at least partially within the housing, and defines a fluid path extending between the proximal face of the housing and the channel of the shaft. An entirety of the fluid path is linear. The cleaning assembly includes a flush port positioned adjacent a proximal face of a housing of the surgical instrument, a flush tube extending distally from the flush port, and a luer fitting configured to selectively engage a proximal portion of the flush port.

In disclosed embodiments, the shaft defines a longitudinal axis, and the fluid path is coaxial with the longitudinal axis.

The disclosure also relates to a method of cleaning a surgical instrument. The method includes uncoupling the surgical instrument from an interface to expose a proximal end of a cleaning assembly. The proximal end of the cleaning assembly disposed at a proximal face of the surgical instrument. The method also includes directing a cleaning solution through a fluid path defined by the cleaning assembly.

In disclosed embodiments, the cleaning solution travels linearly along an entirety of the fluid path.

BRIEF DESCRIPTION OF THE DRAWINGS

Embodiments of the present disclosure are described herein with reference to the accompanying drawings, wherein.

DETAILED DESCRIPTION

Figure 1:
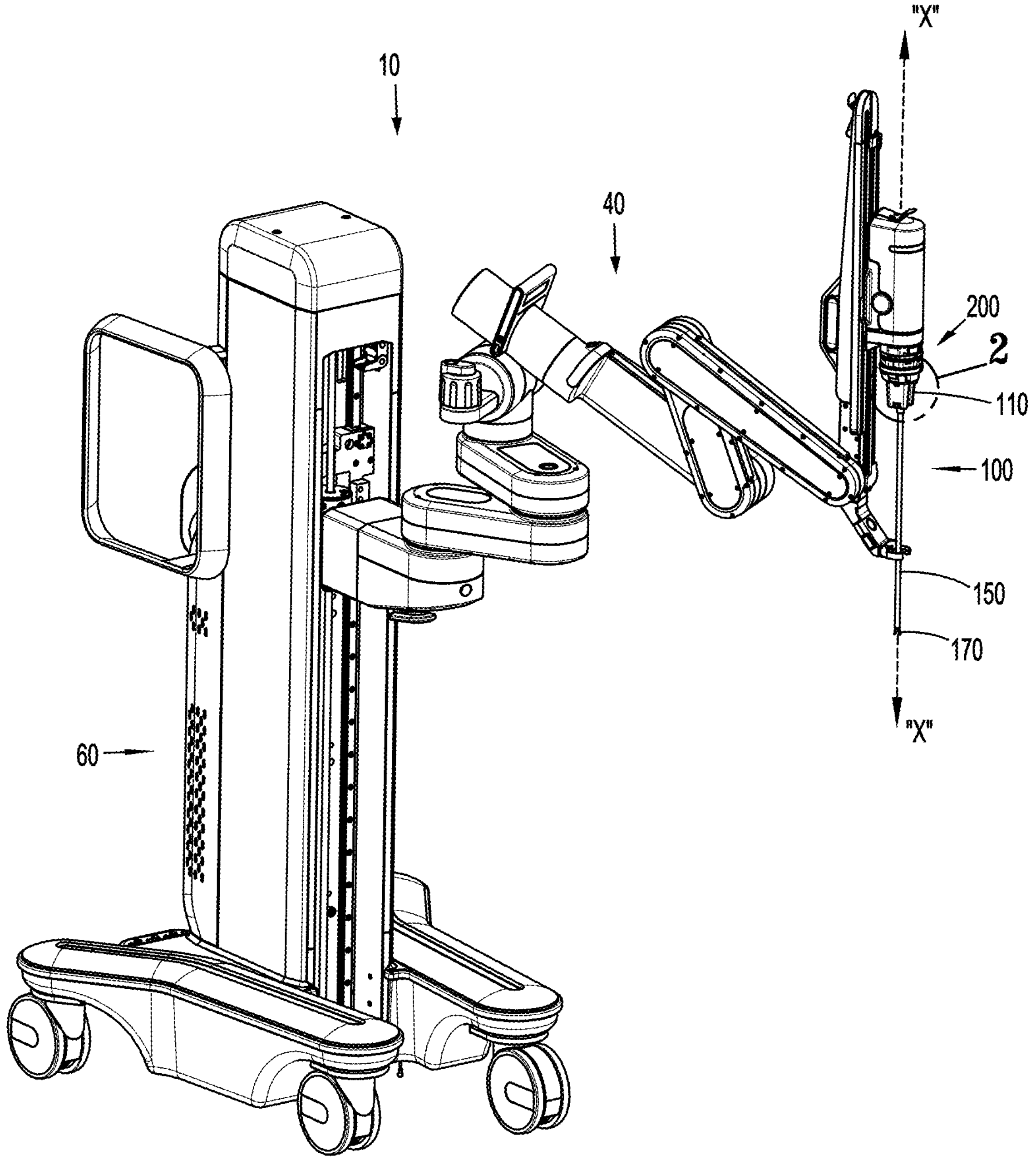
FIG. 1 is a schematic illustration of a robotic surgical system including a robotic arm having a surgical instrument coupled thereto, where the robotic arm is disposed on a movable cart in accordance with embodiments of the present disclosure.
Figure 2:
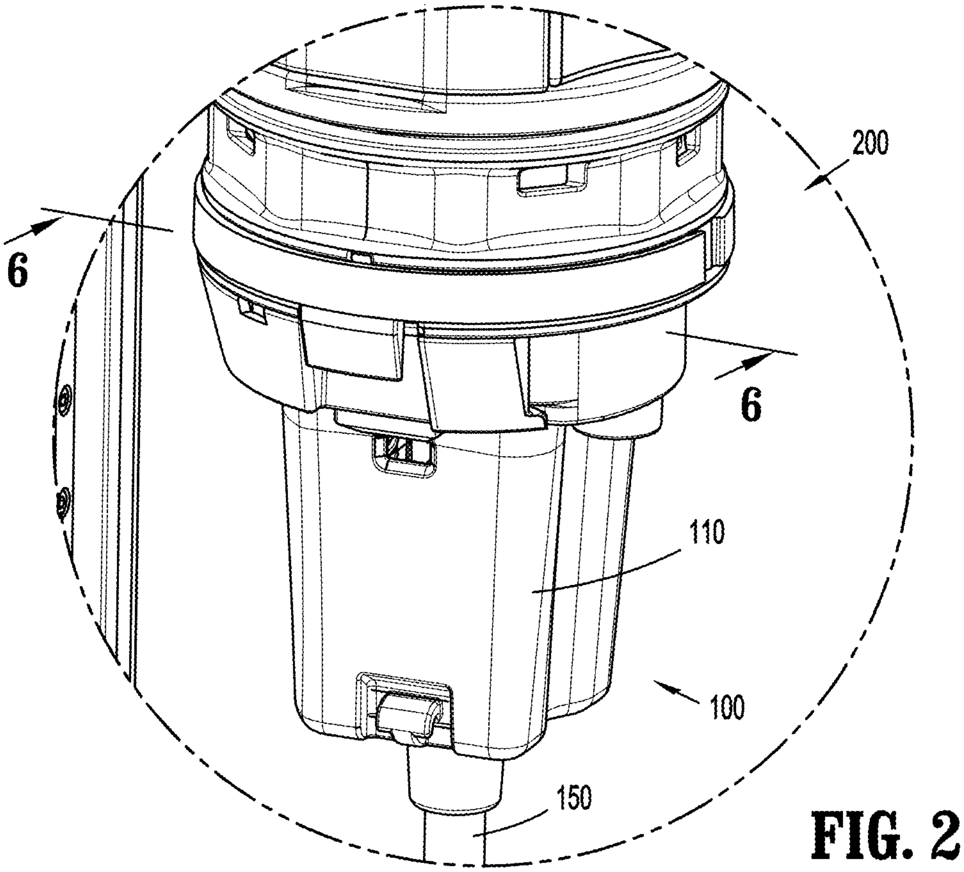
FIG. 2 is an enlarged view of the area of detail indicated in FIG. 1 illustrating the coupling between an interface of the robotic arm and the surgical instrument.

Embodiments of the presently disclosed surgical systems and instruments are described in detail with reference to the drawings, in which like reference numerals designate identical or corresponding elements in each of the several views. As used herein the term "distal" refers to that portion of the surgical instrument, or component thereof, farther from the clinician (and generally closer to the patient), while the term "proximal" refers to that portion of the surgical instrument, or component thereof, closer to the clinician (and generally farther from the patient). As used herein, the terms parallel is understood to include relative configurations that are substantially parallel up to about + or −10 degrees from true parallel.

As used herein, the term "clinician" refers to a doctor, nurse, or other care provider and may include support personnel. In the following description, well-known functions or construction are not described in detail to avoid obscuring the present disclosure in unnecessary detail.

As will be described in detail below, the present disclosure includes a surgical system, such as a robotic surgical system, including a surgical instrument that is engageable with an interface, such as a sterile interface module. When the surgical instrument is engaged with the interface, a seal is formed to prevent or hinder insufflation gases from being able to leak through the surgical instrument. When the surgical instrument is not engaged with the interface, a flush port on a proximal face of the surgical instrument is accessible for cleaning the surgical instrument.

With reference to FIG. 1, a surgical robotic system 10 is shown and includes a robotic arm 40 having an interface 200 (e.g., a sterile interface module), and a surgical instrument 100 removably coupled to the interface 200. The robotic arm 40 is shown coupled to a movable cart 60. While the figures depict a particular type of surgical system (i.e., a robotic surgical system) and a particular type of surgical instrument, the present disclosure encompasses other types of surgical systems (i.e., non-robotic surgical systems) and all suitable surgical instruments such as graspers, sealers, linear staplers, circular staplers, curved staplers, access devices, etc.

Figure 3:
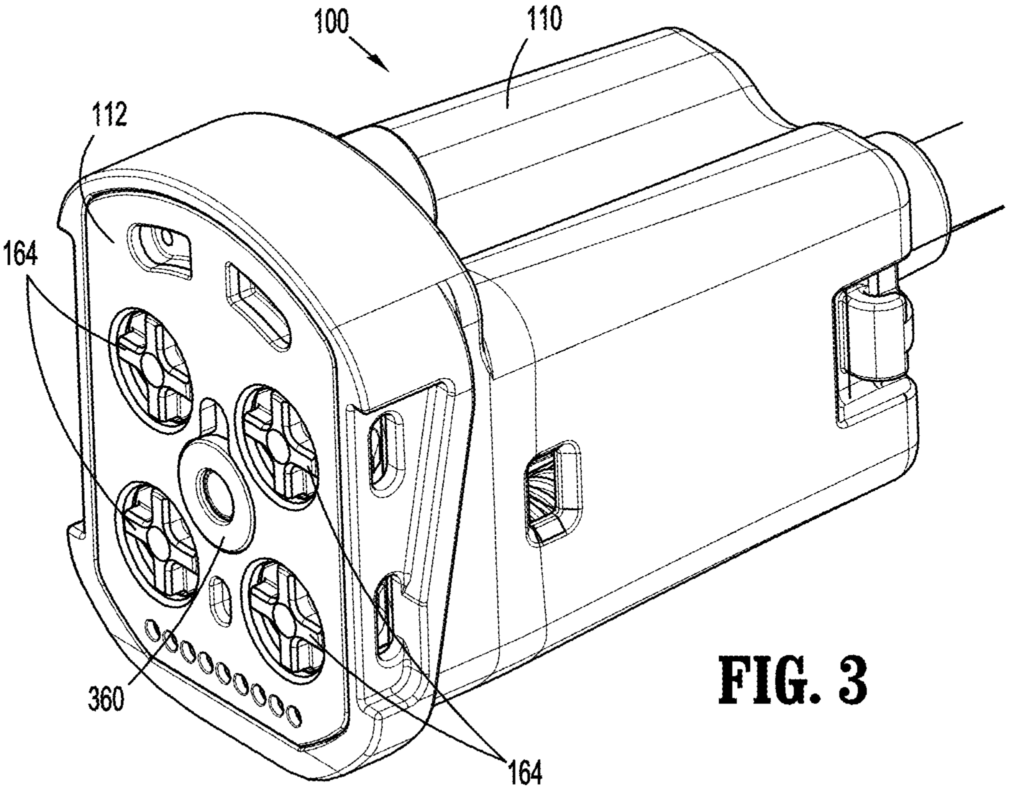
FIG. 3 is a perspective view illustrating a proximal portion of the surgical instrument of FIG. 1 when the surgical instrument is uncoupled from the interface.

As generally shown in FIG. 1, the surgical instrument 100 includes a housing 110, a shaft 150 extending distally from the housing 110 and defining a longitudinal axis "X-X," and an end effector 170 disposed adjacent a distal end of the shaft 150. When the surgical instrument 100 is engaged with the interface 200, a proximal face 112 (FIG. 3, for example) of the housing 110 of the surgical instrument 100 is configured to engage a distal face 202 (FIG. 7, for example) of the interface 200, as discussed in further detail below, or is disposed in face-to-face orientation with one another.

Figure 6:
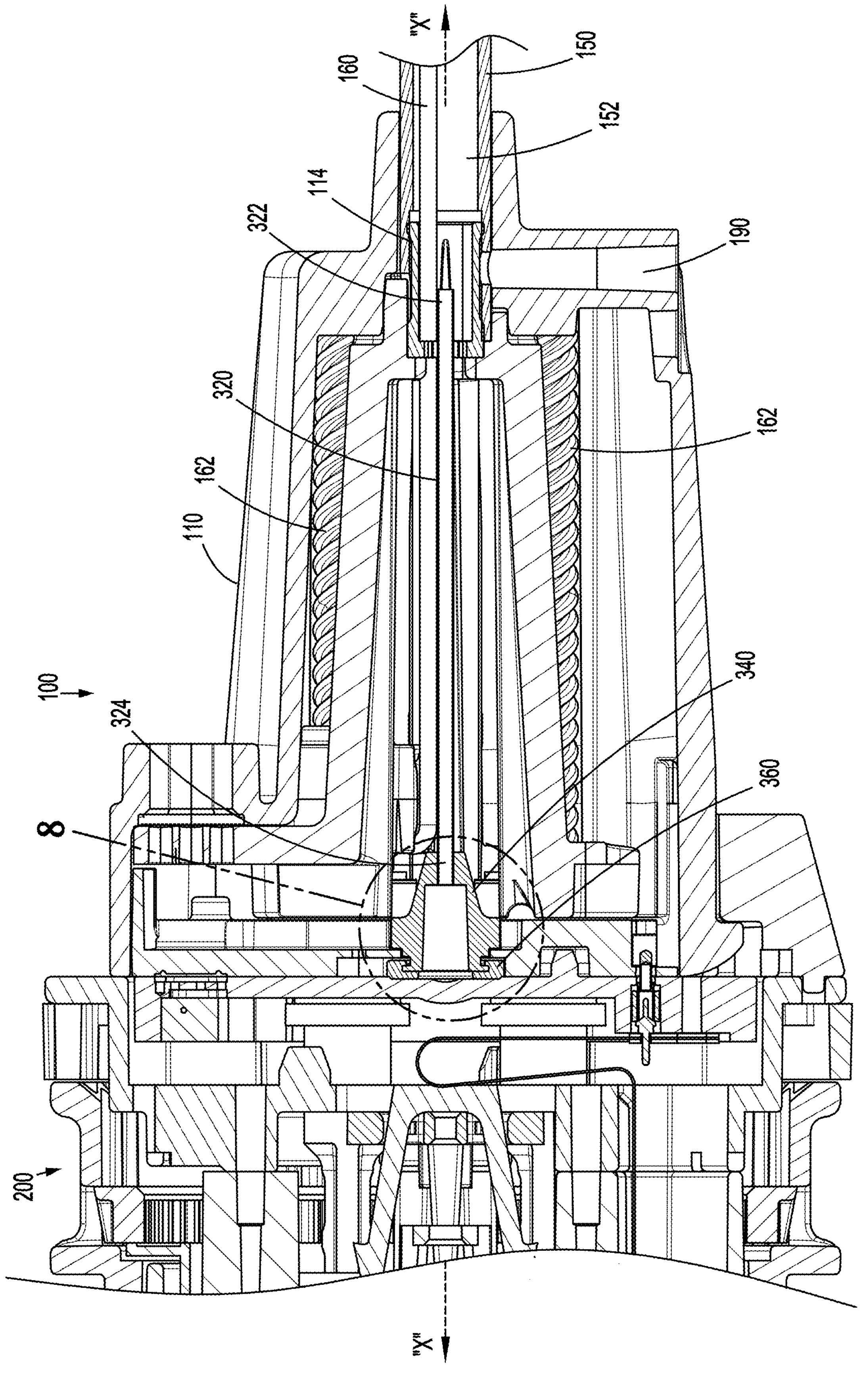
FIG. 6 is a cross-sectional view of a distal portion of the interface coupled to a proximal portion of the surgical instrument of FIG. 1.
Figure 10:
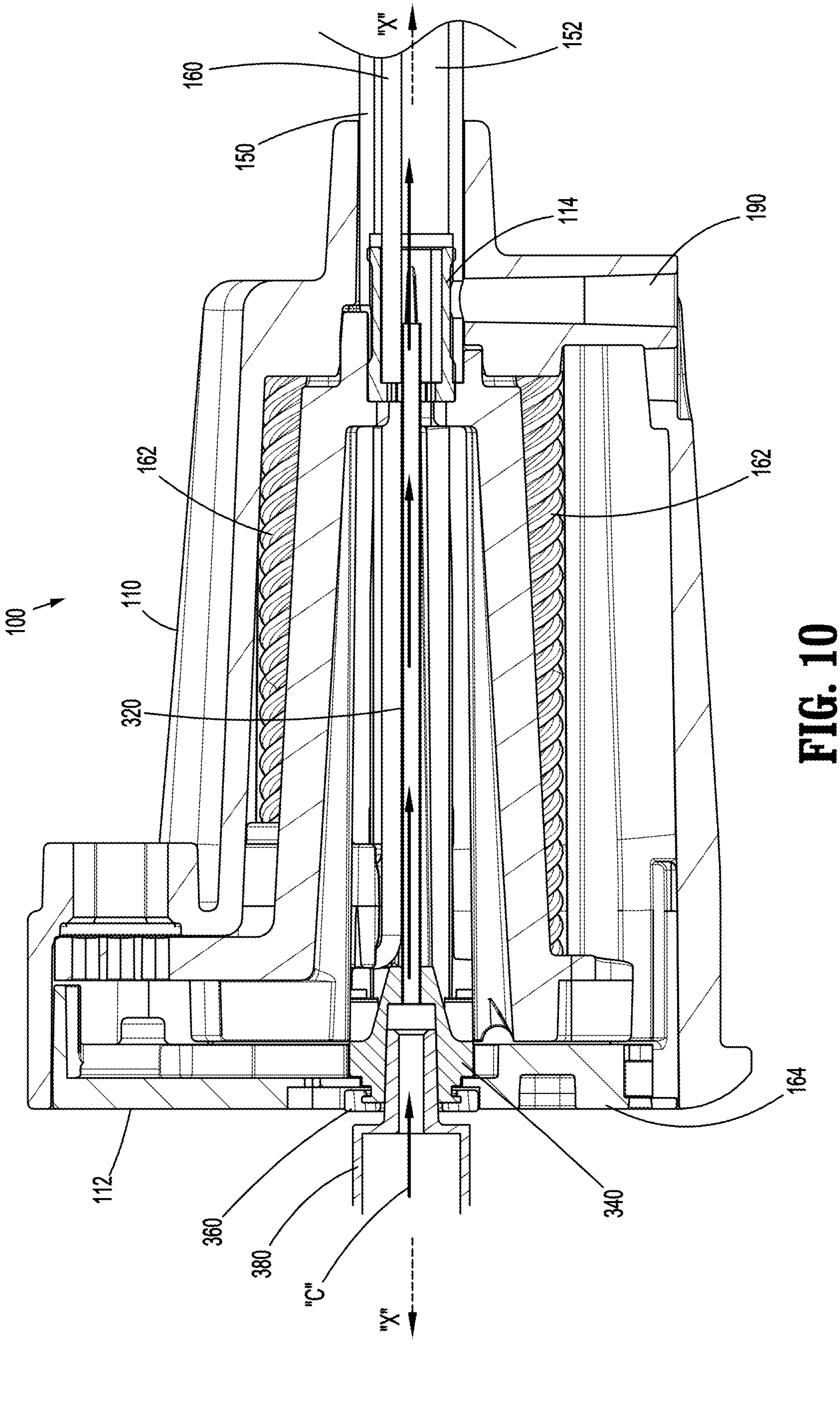
FIG. 10 is a cross-sectional view of a proximal portion of the surgical instrument of FIG. 1 shown uncoupled from the interface and with a luer fitting of the cleaning assembly engaged therewith.
Figure 12:
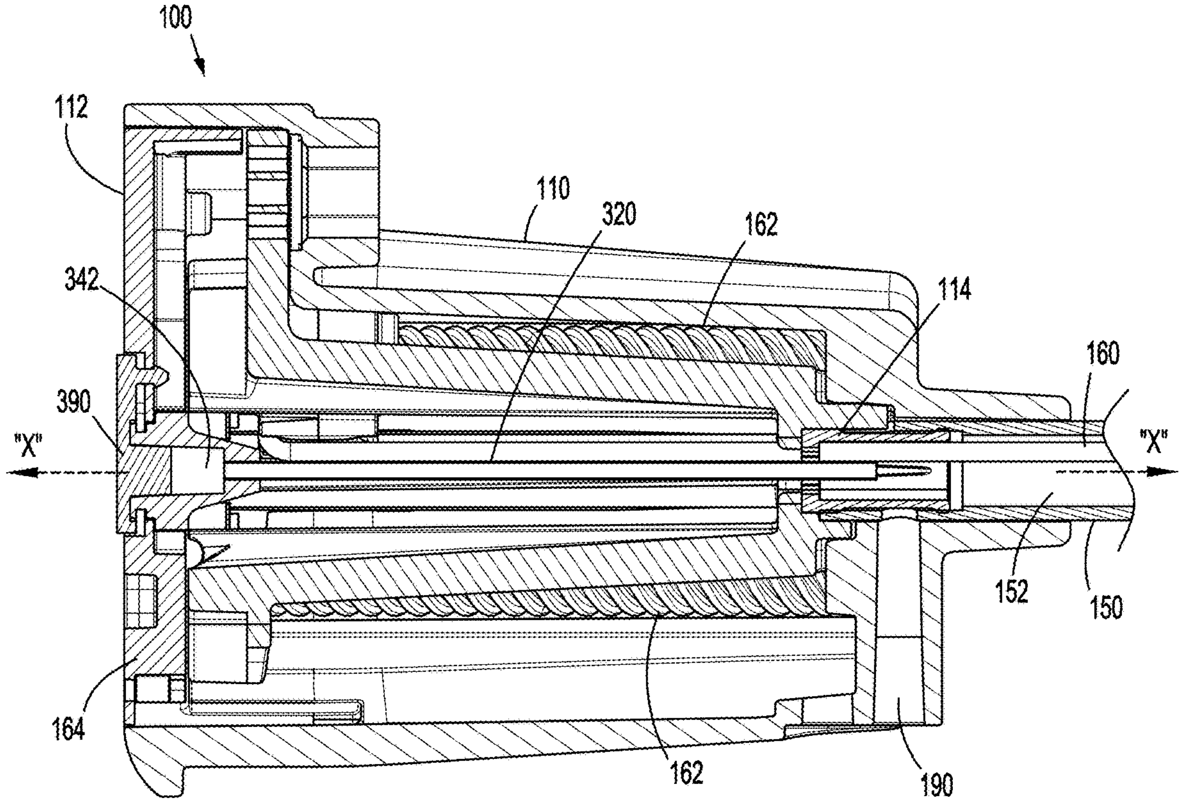
FIG. 12 is a cross-sectional view of a proximal portion of the surgical instrument of FIG. 1 shown uncoupled from the interface and with the plug engaged with a portion of the cleaning assembly.

The end effector 170 is configured to manipulate (e.g., grasp, seal, cut, and/or apply fasteners to) tissue. As shown in FIGS. 6, 10 and 12, at least one drive rod 160 extends through a channel 152 defined by the shaft 150 and is disposed parallel to or coaxial with the longitudinal axis "X-X." A distal portion of the drive rod 160 is disposed in mechanical cooperation with the end effector 170. The drive rod 160 is manipulatable (e.g., longitudinally translatable relative to the shaft 150 and/or rotatable relative to the shaft 150) to cause a desired function of the end effector 170.

Manipulation of the drive rod 160 is accomplished in various manners depending on the type of surgical instrument 100 and/or interface 200 being used. For instance, in the embodiment illustrated in FIGS. 6, 10 and 12, the surgical instrument 100 includes a plurality of drive assemblies 162, where each drive assembly 162 engages the drive rod 160 (or a separate drive rod), for instance. A proximal coupler 164 of each drive assembly 162 extends through and/or is accessible through the proximal face 112 of the housing 110 of the surgical instrument 100 (see FIGS. 3, 4, 9 and 11, for example).

Figure 7:
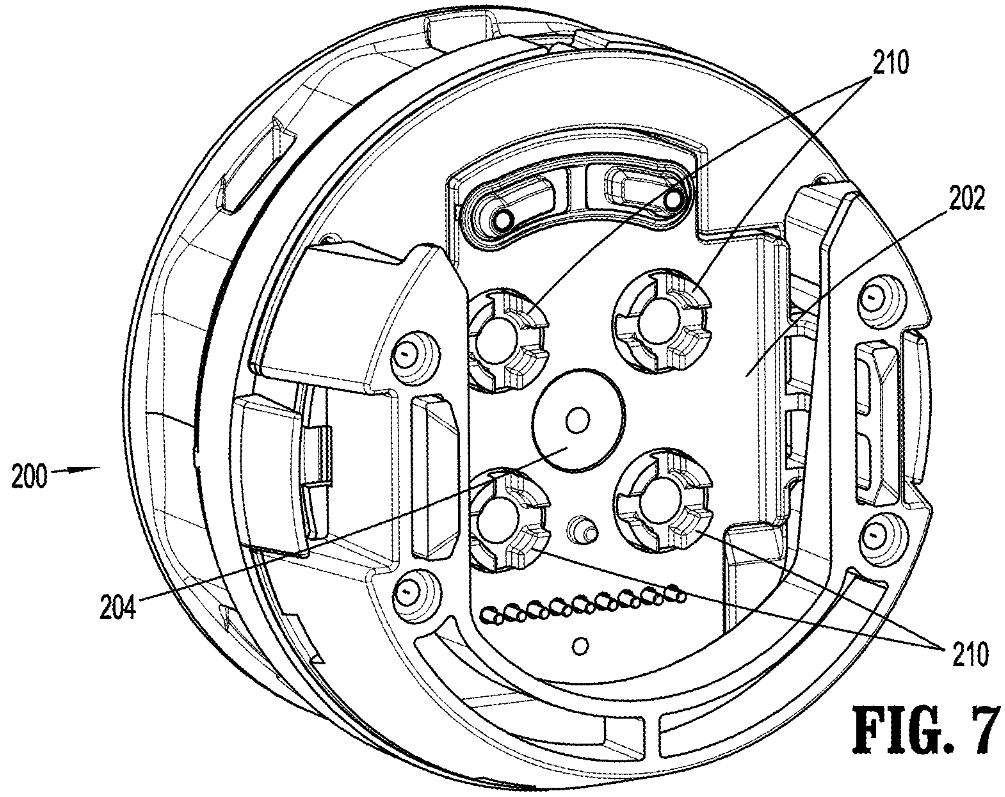
FIG. 7 is a perspective view of the distal portion of the interface of FIG. 1 shown uncoupled from the surgical instrument.

With reference to FIG. 7, the interface 200 includes a plurality of motors 210, with each motor 210 configured to engage the proximal coupler 164 of one drive member 162 when the surgical instrument 100 is engaged with the interface 200. Here, rotation of the motors 210 causes a corresponding rotation of the respective drive members 162. The rotation of each drive member 162 is configured to manipulate its associated drive rod 160, for instance, to effect a function of the end effector 170. Further details of the interface, motors, drive members, etc. are described in U.S. Pat. No. 11,129,685, the entire contents of which are incorporated by reference herein.

Referring to FIGS. 6, 10 and 12, the housing 110 of the surgical instrument 100 also includes a seal member 114 therein. The seal member 114 is configured to prevent or hinder insufflation gas from leaking proximally from within the shaft 150 of the surgical instrument 100 into and/or through the housing 110. The seal member 114 is positioned within a distal portion of the housing 110 and may define a plurality of channels therethrough. For example, a first channel of the seal member 114 may be configured and dimensioned to allow one drive rod 160 to pass therethrough, and a second channel of the seal member 114 may be configured and dimensioned to allow a distal portion 322 of a flush tube 320 to extend at least partially therethrough, as discussed in further detail below. The seal member 114 also includes an additional channel for each additional drive rod 160 to pass at least partially therethrough. (In the illustrated embodiments, the channels are obscured from view by the drive rod 160 and the flush tube 320.) Further, the seal member 114 may include an inlet for fluid communication with an auxiliary cleaning port 190.

Figure 4:
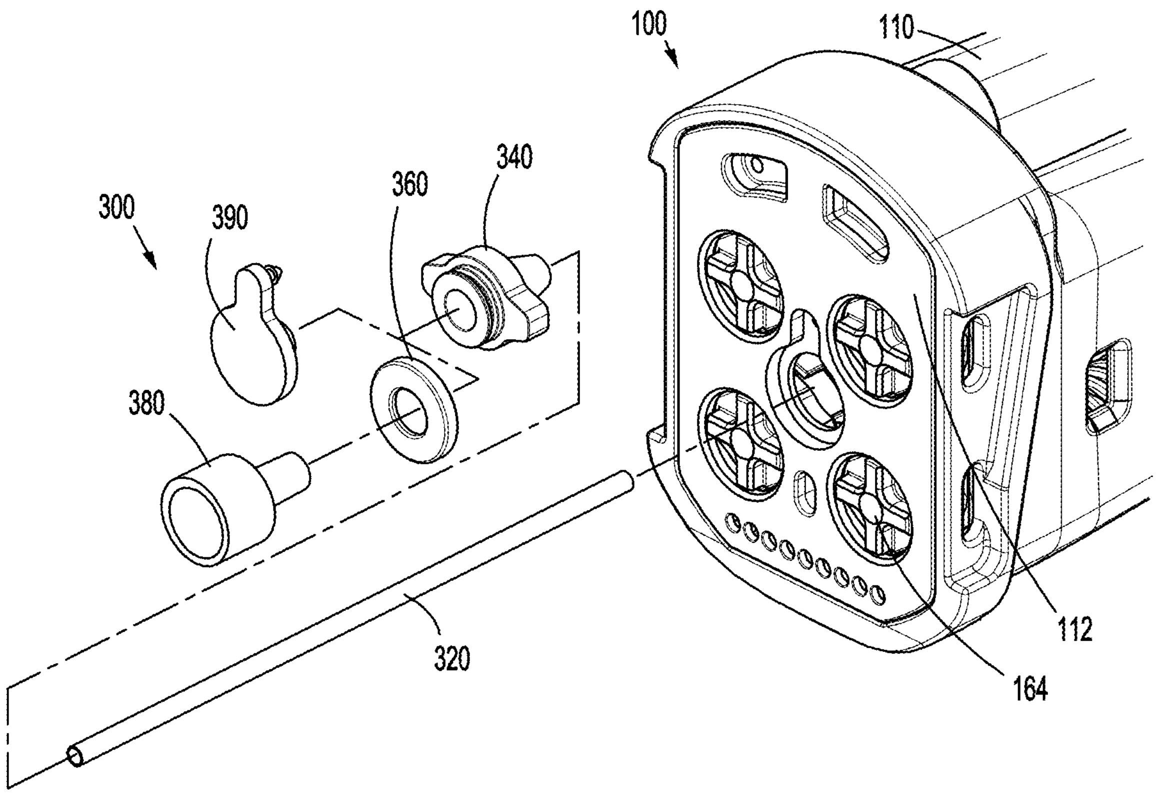
FIG. 4 is a perspective, assembly view of various components of a cleaning assembly and the proximal portion of the surgical instrument of FIG. 1.
Figure 5:
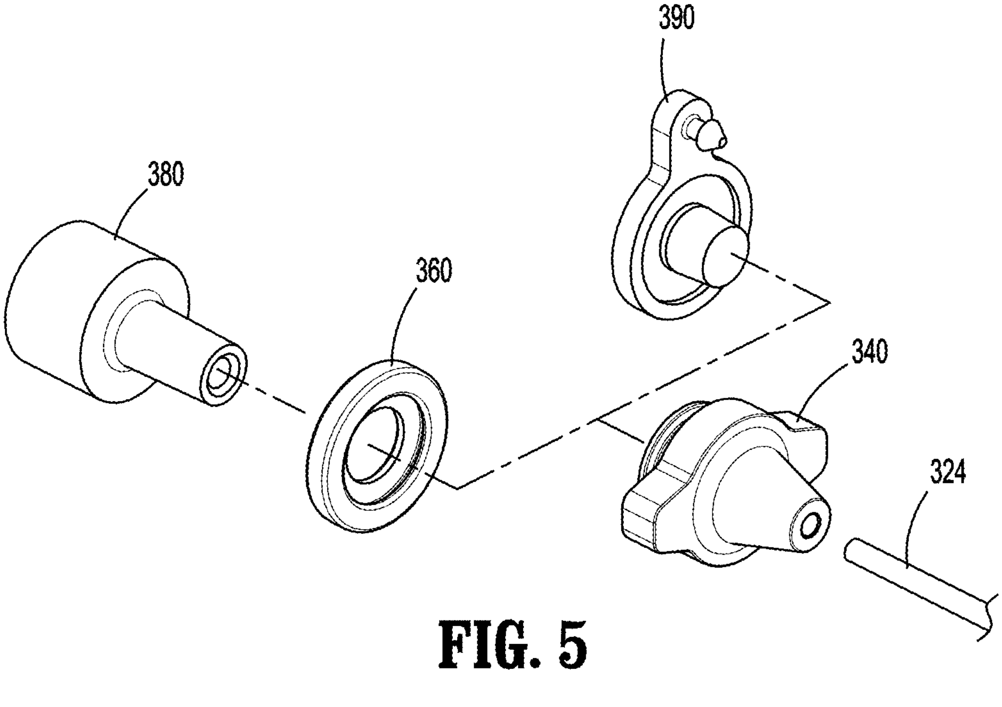
FIG. 5 is a perspective, assembly view of various components of the cleaning assembly of FIG. 4.

Referring now to FIGS. 4 and 5, a cleaning or flushing assembly 300 is shown. The cleaning or flushing assembly 300 includes a flush tube 320, a flush port 340, a gasket 360, a luer fitting 380, and, optionally, a cap, cover or plug 390. Portions of the cleaning or flushing assembly 300 are positioned at least partially within the surgical instrument 100 (e.g., the housing 110) and are configured to allow a cleaning solution (e.g., fluid and/or gas) to be delivered from the proximal face 112 of the housing 110 and into and through the channel 152 defined by the shaft 150 of the surgical instrument 100. Moreover, the cleaning or flushing assembly 300 allows the cleaning solution to bypass all of the internal components disposed within the housing 110 of the surgical instrument 100.

As shown in FIG. 6, a distal end 322 of the flush tube 320 is positioned within the seal member 114 (e.g., within a channel defined therein), and a proximal end 324 of the flush tube 320 is engaged with the flush port 340 disposed adjacent the proximal face 112 of the housing 110. Thus, the flush tube 320 extends through a majority of the housing 110.

In disclosed embodiments, a turbulator may be positioned within the flush tube 320. The turbulator may be in the form of at least one ramp, ridge, deflector, micro channel, and/or ribbon, for example, and may be static or dynamic. In such embodiments, the turbulator is configured to further direct the flow of cleaning fluid, and/or to change the flow of the cleaning fluid from laminar to turbulent, for instance. A turbulent fluid flow may slow down the fluid flow and/or may be configured to target certain portions of the surgical instrument 100 where excess cleaning is desired and/or may be configured to agitate the flow of the cleaning fluid to aid in flushing the shaft 150 of the surgical instrument 100.

Further, while the figures show the flush tube 320 being disposed along or coaxial with the longitudinal axis "X-X," the present disclosure also includes embodiments where the flush tube 320 is offset from the longitudinal axis "X-X" (either parallel to or forming an angle with the longitudinal axis "X-X") while still extending through the proximal face 112 of the housing 110.

Figure 8:
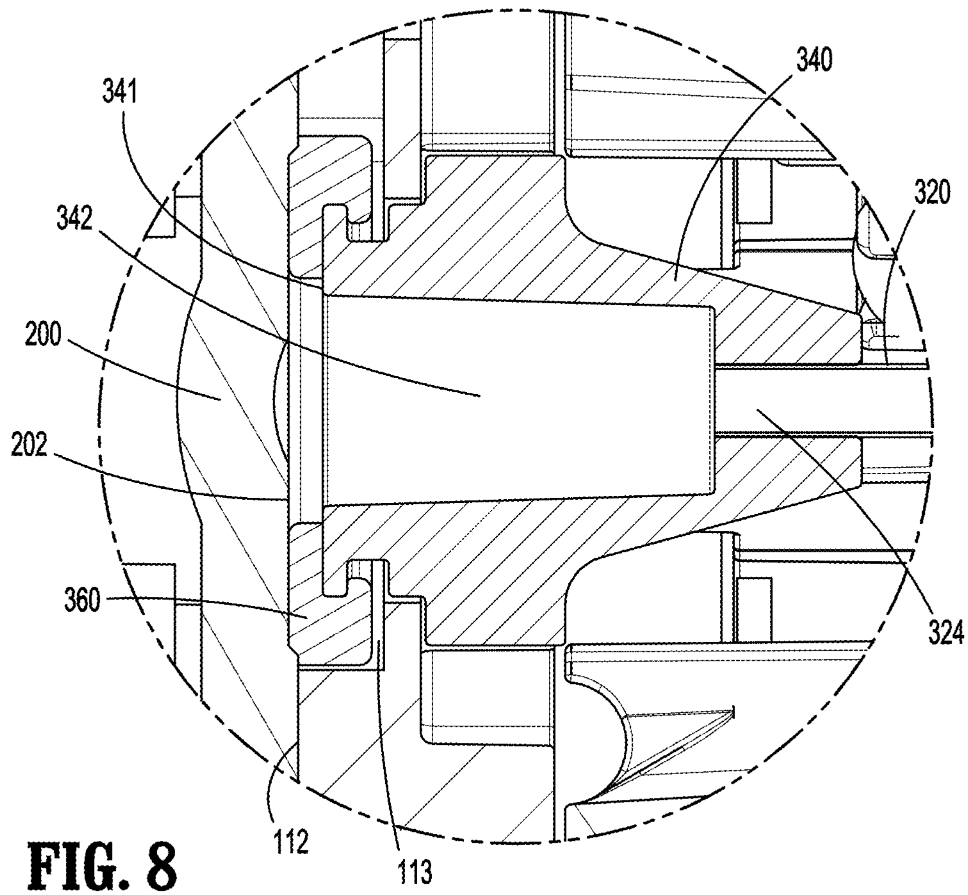
FIG. 8 is an enlarged view of the area of detail indicated in FIG. 6.
Figure 9:
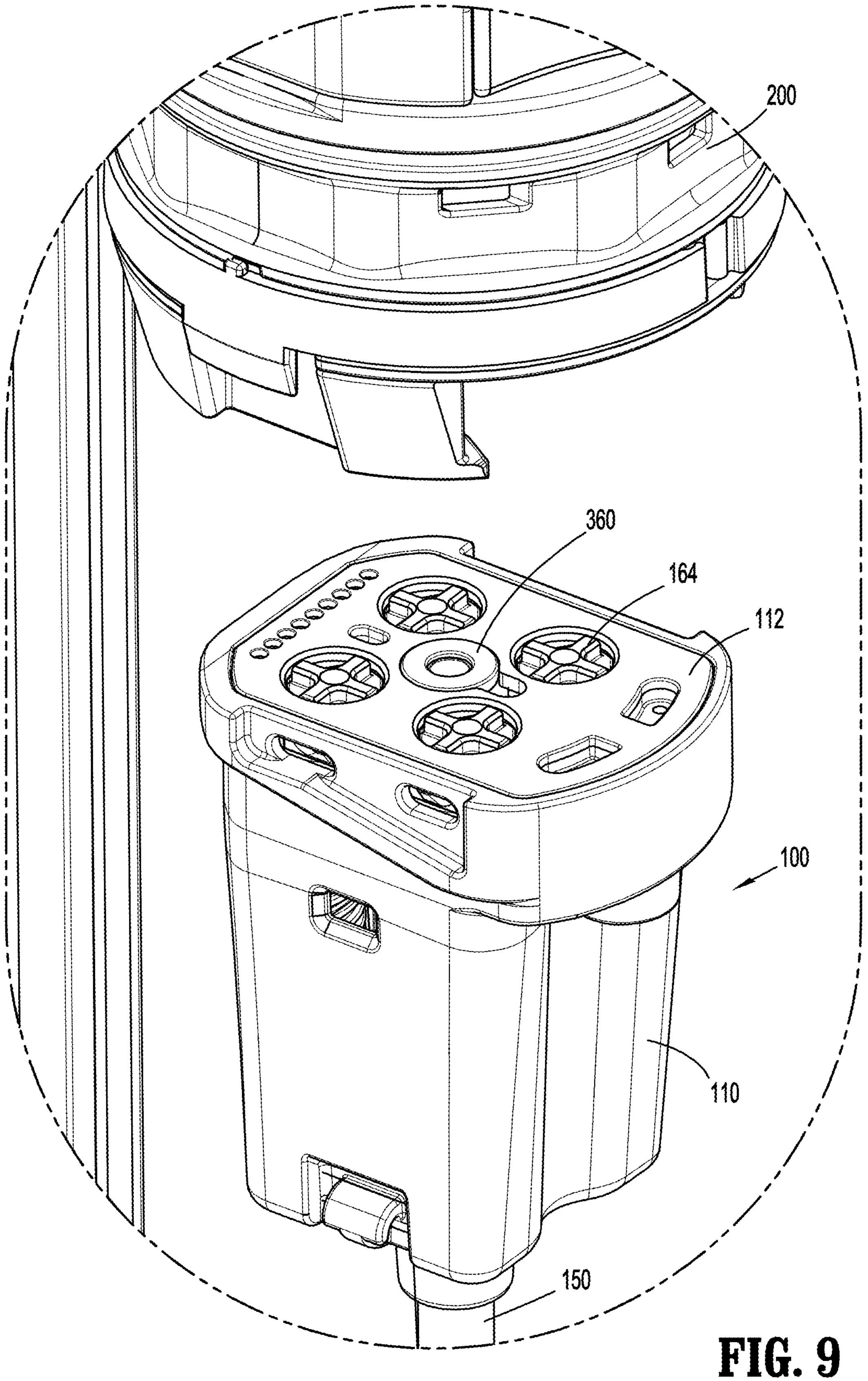
FIG. 9 is a perspective view of a proximal portion of the surgical instrument and a distal portion of the interface of FIG. 1 shown uncoupled from each other.

With reference to FIG. 8, the flush port 340 is shown engaged with the proximal end 324 of the flush tube 320. The flush port 340 defines a cleaning interface 342 in fluid communication with the flush tube 320. The cleaning interface 342 is configured to selectively engage the luer fitting

380 (or a cleaning instrument, nozzle, etc.) to help direct the cleaning solution into the proximal end 324 of the flush tube 320.

With continued reference to FIG. 8, the gasket 360 is shown disposed in contact with a proximal end 341 of the flush port 340. The gasket 360 is positioned at least partially within a groove 113 defined within the proximal face 112 of the housing 110, such that the gasket 360 is either flush with the proximal face 112 of the housing 110, or, as shown in the illustrated embodiment, such that a portion of the gasket 360 protrudes proximally from the proximal face 112 of the housing 110.

The gasket 360 is generally ring-shaped and may be made from a compressible material such as rubber or the like. In use, when the surgical instrument 100 is engaged with the interface 200, the gasket 360 engages the distal face 202 of the interface 200 thereby forming a seal between the surgical instrument 100 and the interface 200. In the illustrated embodiment, where a portion of the gasket 360 protrudes proximally from the proximal face 112 of the housing 110, the interface 200 includes a recess 204 configured to receive the protruding portion of the gasket 360 (see FIG. 7).

Accordingly, when the surgical instrument 100 is engaged with the interface 200, the gasket 360 ensures the insufflation gas cannot escape or leak from the patient and travel between the proximal face 112 of the housing 110 of the surgical instrument 100 and the distal face 202 of the interface 200. Thus, any pressurization within the body cavity is maintained when the surgical instrument 100 is engaged with the interface 200. Conversely, when the surgical instrument 100 is disengaged from the interface 200, the insufflation gas can escape or leak from the body cavity, through the shaft 150 of the surgical instrument 100, through the flush tube 320, and out of the proximal face 112 of the housing 110.

In use, the surgical instrument 100 is coupled to the interface 200 and a surgical task is performed on a patient, for instance. After completion of the surgical task, the user may wish to reuse the surgical instrument 100 to complete the surgical procedure, or to perform another surgical task on a different patient, for example. In either of these instances, it is often desired or necessary to clean within the shaft 150 of the surgical instrument 100. To perform this cleaning operation utilizing the disclosed surgical system 10, the surgical instrument 100 is disengaged (either manually by the user or a clinician, or automatically by the robotic surgical system) from the interface 200, thereby exposing the gasket 360 and the proximal face 112 of the housing 110 of the surgical instrument 100.

Next, the luer fitting 380 is engaged with the flush port 340 (FIG. 10), and a cleaning solution is introduced from the proximal end of the surgical instrument 100. It is envisioned that the engaging of the luer fitting 380 with the flush port 340 and/or the introduction of the cleaning solution into the surgical instrument 100 may be performed either manually by the user or a clinician, or automatically by the robotic surgical system.

The cleaning solution flows generally linearly along a fluid path identified by arrows "C" in FIG. 10. Since the cleaning solution flows generally linearly and does not have to travel through any curves, elbows, bends or tortuous paths prior to reaching the shaft 150 of the surgical instrument 100, the cleaning solution reaches the shaft 150 at a relatively high flow rate (as compared to traveling a more convoluted path) which may be beneficial to ensuring an effective and efficient cleaning of the channel 152 defined by the shaft 150, for instance.

Figure 11:
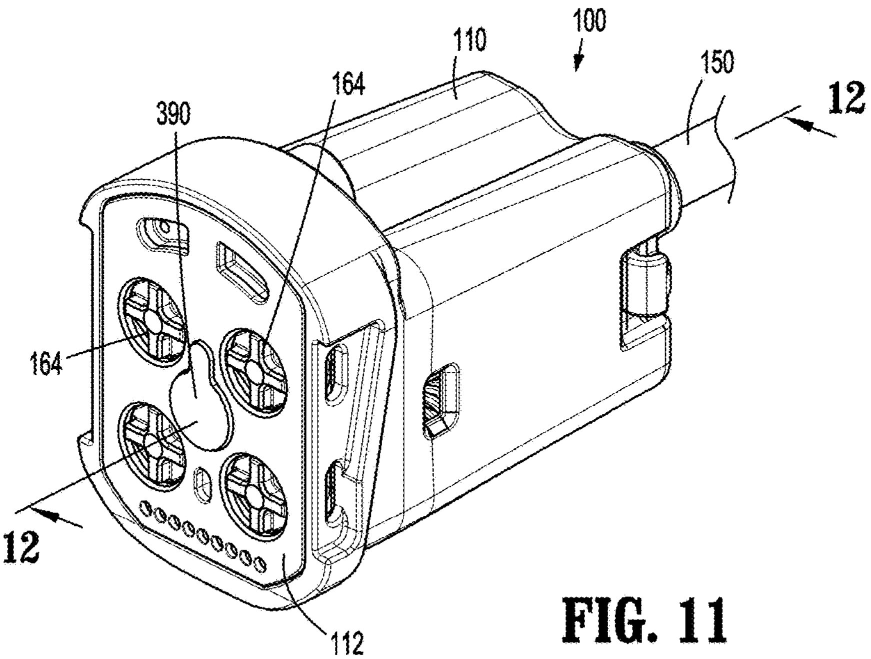
FIG. 11 is a perspective view of a proximal portion of the surgical instrument of FIG. 1 shown uncoupled from the interface and with a plug engaged with a portion of the cleaning assembly.

In the embodiment illustrated in FIGS. 11 and 12, the cleaning assembly 300 includes the plug 390 configured to selectively engage the flush port 340, the gasket 360 and/or the proximal face 112 of the housing 110 (this illustrated embodiment does not include the gasket 360). It is envisioned that the plug 390 is made from rubber, or the like, and engages the cleaning interface 342 of the flush port 340 in a friction-fit manner. It is envisioned that the plug 390 can remain in this position when the surgical instrument 100 is engaged with the interface 200. Here, when cleaning is desired, the surgical instrument 100 is removed from engagement with the interface 200, and the plug 390 is removed from engagement with the flush port 340 to allow a cleaning solution to enter the flush port 340 and the flush tube 320.

When the plug 390 is engaged with the flush port 340, the pressurization within the body cavity can still be maintained even after the surgical instrument 100 and the interface 200 are disengaged from each other. Here, a user would be able to leave the end effector 170 of the surgical instrument 100 within the body cavity, for instance, while switching the interface 200 that is engaged with the surgical instrument 100. To clean the surgical instrument 100 in this embodiment, the plug 390 is removed from engaged with the flush port 340, the luer fitting 380 is positioned in engagement with the flush port 340, and a cleaning solution is introduced from the proximal end of the surgical instrument 100.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 13:
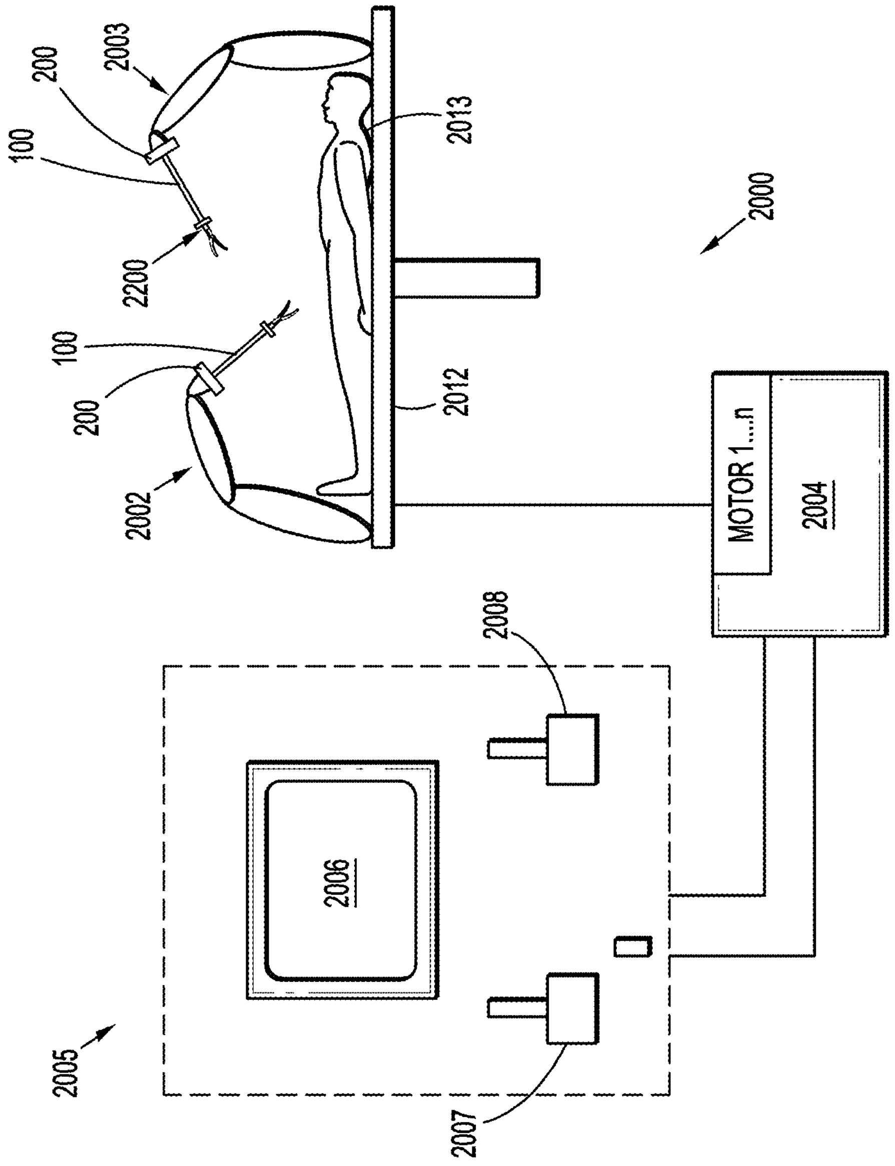
FIG. 13 is a schematic illustration of a robotic surgical system configured for use in accordance with the disclosure.

With reference to FIG. 13, a surgical system, such as, for example, a robotic surgical system is shown generally as surgical system 2000 and is usable with the surgical instrument 100 and/or the interface 200, or portions thereof, of the disclosure. Surgical system 2000 generally includes a plurality of robotic arms 2002, 2003, a control device 2004, and an operating console 2005 coupled with control device 2004. Operating console 2005 includes a display device 2006, which is set up in particular to display three-dimensional images; and manual input devices 2007, 2008, by means of which a person (not shown), for example a surgeon, is able to telemanipulate robotic arms 2002, 2003 in a first operating mode, as known in principle to a person skilled in the art.

Each of the robotic arms 2002, 2003 is composed of a plurality of members, which are connected through joints. System 2000 also includes an instrument drive unit 2200 connected to distal ends of each of robotic arms 2002, 2003. The surgical grasping device 500, or portions thereof, may be attached to the instrument drive unit 2200, in accordance with any one of several embodiments disclosed herein, as will be described in greater detail below.

Robotic arms 2002, 2003 may be driven by electric drives (not shown) that are connected to control device 2004. Control device 2004 (e.g., a computer) is set up to activate the drives, in particular by means of a computer program, in such a way that robotic arms 2002, 2003, their instrument drive units 2200 and thus the surgical grasping device 500 (including the end effector 530) execute a desired movement according to a movement defined by means of manual input devices 2007, 2008. Control device 2004 may also be set up in such a way that it regulates the movement of robotic arms 2002, 2003 and/or of the drives.

Surgical system 2000 is configured for use on a patient 2013 lying on a patient table 2012 to be treated in a minimally invasive manner by means of the surgical instrument 100. Surgical system 2000 may also include more than two robotic arms 2002, 2003, the additional robotic arms likewise being connected to control device 2004 and being telemanipulatable by means of operating console 2005.

Reference may be made to U.S. Pat. No. 8,828,023, entitled "Medical Workstation," the entire content of which is incorporated herein by reference, for a detailed discussion of the construction and operation of surgical system 2000.

It should be understood that the foregoing description is only illustrative of the disclosure. Various alternatives and modifications can be devised by those skilled in the art without departing from the disclosure. Accordingly, this disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical instrument, comprising:
a housing including a proximal face;
a shaft extending distally from the housing and defining a channel having a longitudinal axis;
an end effector disposed adjacent a distal end of the shaft, the end effector configured to manipulate tissue; and
a cleaning assembly disposed at least partially within the housing, the cleaning assembly defining a fluid path having a fluid path axis that is colinear with the longitudinal axis of the channel and that extends between the proximal face of the housing and the channel of the shaft, wherein the cleaning assembly includes a gasket formed of compressible material and supported on and projecting from the proximal face of the housing, and wherein the gasket surrounds a proximal opening of the fluid path, whereby the gasket forms a seal between the surgical instrument and an interface when the surgical instrument is connected to the interface.

2. The surgical instrument according to claim 1, wherein the fluid path is linear along its entire length.

3. The surgical instrument according to claim 1, wherein the fluid path is linear along an entire length of the cleaning assembly, the housing and the shaft.

4. The surgical instrument according to claim 1, wherein the gasket is disposed at least partially within a groove defined on the proximal face of the housing.

5. The surgical instrument according to claim 1, wherein the cleaning assembly includes a flush port disposed adjacent a proximal end of the fluid path, wherein the flush port defines a portion of the fluid path, wherein the flush port is contained within the housing, and wherein the fluid path is linear along an entire length of the flush port of the cleaning assembly, the housing and the shaft.

6. The surgical instrument according to claim 5, wherein the cleaning assembly includes a luer fitting configured to selectively engage the flush port.

7. The surgical instrument according to claim 5, wherein the cleaning assembly includes a flush tube extending linearly within a majority of the housing, wherein the flush tube defines a flush tube axis which is colinear with the fluid path axis.

8. The surgical instrument according to claim 1, further including a seal disposed adjacent a proximal portion of the shaft.

9. The surgical instrument according to claim 8, wherein the cleaning assembly includes a flush tube extending at least partially through the seal.

10. The surgical instrument according to claim 8, wherein the cleaning assembly includes a flush port disposed adjacent a proximal end of the fluid path.

11. The surgical instrument according to claim 10, wherein the cleaning assembly includes a flush tube extending between the flush port and the seal.

12. The surgical instrument according to claim 1, wherein the cleaning assembly includes a plug configured to selectively occlude the proximal opening of the fluid path.

13. The surgical instrument according to claim 1, wherein the housing is configured to couple to the interface, wherein when the interface is coupled to the housing, a proximal opening of the fluid path is occluded by the interface.

14. The surgical instrument according to claim 1, further including a drive member disposed at least partially within the housing, and a drive rod disposed at least partially within the shaft, wherein actuation of the drive member is configured to manipulate the drive rod to effect a function of the end effector.

15. The surgical instrument according to claim 14, wherein the cleaning assembly includes a flush tube extending linearly within a majority of the housing, a proximal end of the drive rod is disposed proximally of a distal end of the flush tube.

16. A cleaning assembly for use with a surgical instrument having a longitudinal axis, the cleaning assembly comprising:
a flush port configured for positioning on a proximal face of a housing of the surgical instrument;
a flush tube extending distally from the flush port; and
a gasket formed of compressible material and supported on and projecting from the proximal face of the housing,
wherein the cleaning assembly defines a fluid path through the housing of the surgical instrument, wherein the fluid path defines a fluid path axis that is colinear with the longitudinal axis of the surgical instrument, and wherein the gasket surrounds a proximal opening of the fluid path, whereby the gasket forms a seal between the surgical instrument and an interface when the surgical instrument is connected to the interface.

17. The cleaning assembly according to claim 16, wherein the gasket is configured to engage the proximal portion of the flush port.

18. The cleaning assembly according to claim 16, further including a plug configured to selectively engage the proximal portion of the flush port and occlude the fluid path.

19. A surgical instrument, comprising:
a housing including a proximal face;
a shaft extending distally from the housing and defining a channel having a longitudinal axis; and
a cleaning assembly disposed at least partially within the housing, the cleaning assembly defining a fluid path having a fluid path axis that is colinear with the longitudinal axis of the channel and that extends between the proximal face of the housing and the channel of the shaft, an entirety of the fluid path is linear, the cleaning assembly including:
  a flush port positioned adjacent a proximal face of a housing of the surgical instrument;
  a flush tube extending distally from the flush port; and
  a gasket formed of compressible material and supported on and projecting from the proximal face of the housing, wherein the gasket surrounds the entry of the fluid path, whereby the gasket forms a seal between the surgical instrument and an interface when the surgical instrument is connected to the interface.

20. The surgical instrument according to claim 19, wherein the fluid path is linear along an entire length of the cleaning assembly, the housing and the shaft.

* * * * *